(12) United States Patent
Tatum et al.

(10) Patent No.: US 11,875,702 B2
(45) Date of Patent: Jan. 16, 2024

(54) FRACTURE REDUCTION SIMULATOR

(71) Applicant: University of Iowa Research Foundation, Iowa City, IA (US)

(72) Inventors: Marcus Tatum, Iowa City, IA (US); Geb W. Thomas, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 17/848,810

(22) Filed: Jun. 24, 2022

(65) Prior Publication Data

US 2022/0327963 A1 Oct. 13, 2022

Related U.S. Application Data

(63) Continuation of application No. 17/044,025, filed as application No. PCT/US2019/026030 on Apr. 5, 2019, now Pat. No. 11,403,966.

(60) Provisional application No. 62/654,382, filed on Apr. 7, 2018.

(51) Int. Cl.
*G09B 23/30* (2006.01)
*G09B 9/00* (2006.01)
*G01R 33/02* (2006.01)

(52) U.S. Cl.
CPC ............... *G09B 23/30* (2013.01); *G09B 9/00* (2013.01); *G01R 33/0206* (2013.01)

(58) Field of Classification Search
CPC .......... G09B 23/30; G09B 9/00; G09B 23/28; G09B 23/32; G01R 33/0206
See application file for complete search history.

(56) References Cited

U.S. PATENT DOCUMENTS

| | | | |
|---|---|---|---|
| 4,106,219 | A | 8/1978 | Schneider et al. |
| 4,802,858 | A | 2/1989 | Lindskog et al. |
| 5,279,309 | A | 1/1994 | Taylor et al. |
| 5,607,311 | A | 3/1997 | Browne-Wilkinson |
| 7,840,254 | B2 | 11/2010 | Glossop |
| 8,021,162 | B2 | 9/2011 | Sui |
| 2002/0077543 | A1 | 6/2002 | Grzeszczuk et al. |
| 2004/0030245 | A1 | 2/2004 | Noble et al. |

(Continued)

FOREIGN PATENT DOCUMENTS

EP 1205295 A1 5/2002

OTHER PUBLICATIONS

International Preliminary Report on Patentability, PCT/US2019/026030, dated Oct. 22, 2020, 6 Pages.

(Continued)

*Primary Examiner* — Timothy A Musselman
(74) *Attorney, Agent, or Firm* — Goodhue, Coleman & Owens, P.C.

(57) ABSTRACT

A system for simulating surgery includes an electromagnetic tracking system comprising an emitter and a plurality of electromagnetic sensors and a plurality of model bone fragments, each of the model bone fragments operatively connected to one of the plurality of electromagnetic sensors. A method for simulating surgery includes electromagnetically tracking position of a plurality of model bone fragments and a model bone shaft using an electromagnetic tracking system and displaying virtual fluoroscopic images based on sensed position of the model bone fragments and the model bone shaft.

20 Claims, 12 Drawing Sheets

(56) References Cited

U.S. PATENT DOCUMENTS

| | | |
|---|---|---|
| 2005/0058363 A1 | 3/2005 | Florent et al. |
| 2005/0142525 A1 | 6/2005 | Cotin et al. |
| 2007/0212672 A1 | 9/2007 | McAllister et al. |
| 2011/0097696 A1 | 4/2011 | Cuervo et al. |
| 2014/0180416 A1 | 6/2014 | Radojicic |
| 2018/0218649 A1* | 8/2018 | Wucherer ............ G09B 23/286 |
| 2018/0286287 A1 | 10/2018 | Razzaque |

OTHER PUBLICATIONS

International Search Report & Written Opinion, PCT/US2019/026030, dated Jun. 24, 2019, 10 Pages.

* cited by examiner

FRACTURE REDUCTION SIMULATOR

PRIORITY STATEMENT

This application is a continuation of Non-Provisional patent application Ser. No. 17/044,025, filed Sep. 30, 2020 which is a National Phase of PCT Application No. PCT/US19/26030, filed Apr. 5, 2019 which claims priority to U.S. Utility Application No. 62/654,382, filed Apr. 7, 2018, all titled "Fracture Reduction Simulator", all of which are hereby incorporated by reference in its entirety.

GRANT REFERENCE

This invention was made with government support R18 HS025353 awarded by the Agency for Healthcare Research and Quality. The Government has certain rights in the invention.

FIELD OF THE INVENTION

The present invention relates to orthopedic surgery simulation. More particularly, but not exclusively, the present invention relates to a simulation platform to train and assess orthopedic surgical skills, including fracture reduction.

BACKGROUND

Training orthopedic surgical residents or practicing orthopedic surgeons to acquire or improve surgical skills remains problematic for a variety of reasons. Although surgical simulators of various types exist, such simulators may be of limited functionality and do not address the specific challenge of reducing a fracture. Fracture reduction involves decisions about how to apply clamping and temporary fixation approaches in order to overcome mechanical resistance and mechanical manipulations to adjust the position of bone fragments.

Examples of prior art systems may rely on virtual reality and complete virtual environments without physical models or tools and instead may use tracked grips to simulate tools. Such systems lack the realistic feedback that actual surgical tools and models give. They also do not allow for tools such as a clamping mechanism to be used with the necessary degree of realism to be an effective training tool in the task of fracture reduction. Indeed, a large part of learning fracture reduction techniques is understanding the direct haptic feedback required to correctly align the fragments while applying an appropriate amount of pressure.

A further skill needed in performing facture reduction techniques is the hand-eye coordination used in interpreting the shadows in fluoroscopic images as the fragments are moved into correct position. What is needed is a simulator for orthopaedic fractures.

SUMMARY

Therefore, it is a primary object, feature, or advantage of the present invention to improve over the state of the art.

It is a further object, feature, or advantage to provide a simulator which may be used for the training and evaluation of orthopedic medical residents or practicing surgeons on the surgical task of fracture reduction.

It is a still further object, feature or advantage to provide a low stress, repeatable fraction reduction simulation that can provide instant feedback on performance.

It is still further object, feature, or advantage to provide a simulator for orthopaedic fractures.

It is a further object, feature, or advantage of the present invention to provide for a surgical simulator which allows a surgical resident or other user to practice aligning irregular shapes in 3D space while relying on 2D images.

It is a still further object, feature, or advantage of the present invention to provide a surgery simulator which allows surgical residents, practicing surgeons, or other users to practice using actual physical surgical instruments such as a surgical wire or tenaculum or simulated versions of such instruments.

Another object, feature, or advantage is to provide a simulator which tracks bone fragments.

A still further object, feature, or advantage is to connect sensors to bone fragments in a manner which securely and precisely affixes the sensors.

Another object, feature, or advantage is to provide a surgical simulator which may be used to assess surgical skill.

Yet another object, feature, or advantage is to compare surgical techniques for a particular fracture pattern.

A further object, feature, or advantage is to provide for evaluating treatment approaches such as different surgical designs.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a system for simulating surgery is provided. The system includes an electromagnetic tracking system comprising an emitter and a plurality of electromagnetic sensors and a plurality of model bone fragments, each of the model bone fragments operatively connected to one of the plurality of electromagnetic sensors. Each of the model bone fragments may include one or more slots and each of the model bone fragments may be operatively connected to the one of the plurality of electromagnetic sensors using at least one screw-in key, each of the at least one screw-in-key attached to a corresponding one of the one or more slots. The system may further include a display system in operative communication with the electromagnetic tracking system for displaying virtual fluoroscopic images based on a sensed position of the model bone fragments. The model bone shaft may have an additional electromagnetic sensor associated therewith. The system may further include a soft tissue envelope for positioning around the plurality of model bone fragments and the model bone shaft.

According to another aspect, a method for simulating surgery is provided. The method includes steps of electromagnetically tracking position of a plurality of model bone fragments and a model bone shaft using an electromagnetic tracking system and displaying virtual fluoroscopic images based on sensed position of the model bone fragments and the model bone shaft. The electromagnetically tracking position step may occur while a user manipulates one or more of the plurality of model bone fragments using a physical surgical instrument such as a surgical wire and a tenaculum. The method may also include preparing for the surgery by placing the model fragments at predetermined locations and positioning a soft tissue envelope around the plurality of model bone fragments and the model bone shaft.

According to another aspect, a method for simulating surgery may include providing a system for simulating surgery, the system including an electromagnetic tracking system having an emitter and a plurality of electromagnetic sensors and a plurality of model bone fragments and a model bone shaft, each of the model bone fragments operatively connected to one of the plurality of electromagnetic sensors or the model bone shaft. The method may further include electromagnetically tracking position of the plurality of model bone fragments and the model bone shaft using the electromagnetic tracking system. The method may further provide for displaying virtual fluoroscopic images based on sensed position of the model bone fragments and the model bone shaft.

According to another aspect, a system for simulating surgery involving a bone fracture reduction includes a tracking system and a plurality of model bone fragments. The tracking system provides for locating position and orientation of each of the plurality of model bone fragments.

BRIEF DESCRIPTION OF THE DRAWINGS

Illustrated embodiments of the disclosure are described in detail below with reference to the attached drawing figures, which are incorporated by reference herein.

DETAILED DESCRIPTION

A simulation platform may be used to train and assess orthopedic resident surgical skills, including fracture reduction. The simulator may use physical fracture models, real surgical tools, an electromagnetic tracking system, and software to display virtual x-ray images to a display such as a laptop screen. The physical fracture model may be based on a consumer synthetic bone fracture model buried in a synthetic soft tissue model (such as available from SawBones, Vashion Island, WA) or may be 3D printed or otherwise made. The electromagnetic sensors may be attached to specialized bone fragments that are placed in the soft tissue and covered from sight. A housing and mounting system may secure the fracture model to a base and hide the tracking system from sight. In one training module, a student may be tasked with re-assembling bone fragments into a correct alignment. This is done using real surgical tools or physical representations of surgical tools to manipulate the fragments and virtual x-rays to determine the fragment locations. The physical fragment and tool locations may be mapped using the electromagnetic tracking system to correctly display the fragment and tool locations. This is a useful simulator because the act of aligning irregular shapes in 3D space, relying on 2D x-rays is a very difficult and non-trivial action that takes time and training to learn. Surgical students may think they have fragments correctly aligned, when in fact they are misaligned. This mistake may even not be noticeable to the individual and later manifest in improperly set fractures.

Figure 1:
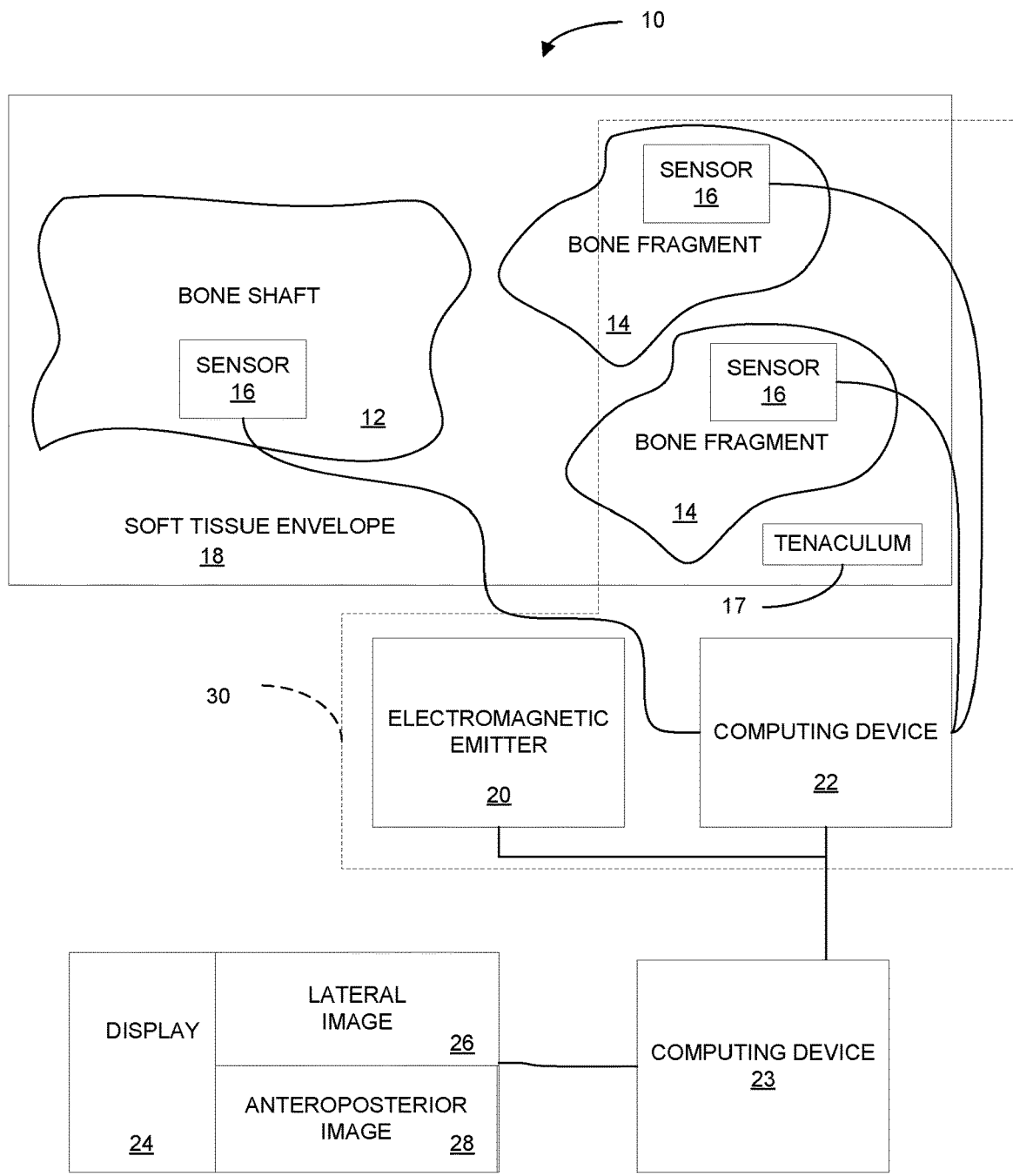
FIG. 1 is a block diagram illustrating one example of a system.

FIG. 1 illustrates one example of a system 10 for simulating surgery. As shown in FIG. 1 there is an electromagnetic tracking system 30 which includes an emitter 20 and a plurality of electromagnetic sensors 16. There are also a plurality of model bone fragments 14. Each of the model bone fragments 14 is operatively connected to one of the sensors 16. The sensors 16 may be attached in various ways including using at least one screw-in key positioned on the sensor 16 and at least one corresponding slot on the model bone fragment 14. A model bone shaft 12 is also shown which may also include an electromagnetic sensor 16. A soft tissue envelope 18 may surround the model bone shaft 12 and the model bone fragments 14.

The electromagnetic emitter 20 is positioned sufficiently close to the bone shaft 12, model bone fragments 14 and the attached sensors 16 to provide accurate tracking of position of the bone shaft 12 and the model bone fragments 14. The electromagnetic tracking system may provide for 6DOF (Degrees-Of-Freedom) tracking so that both position and orientation are tracked. In other words, x, y, and z coordinates of a space are tracked as well as yaw, pitch, and roll. Moreover, because electromagnetic tracking is used, limitations associated with line-of-sight tracking are eliminated. Furthermore, issues associated with drift are not encountered as may be the case if inertial sensors were positioned on the bone shaft and bone fragments instead. Finally, the need for complex calibration procedures are avoided when the electromagnetic tracking system is used.

A computing device 22 is operatively connected to the emitter 20 and the sensors 16 and be a part of the electromagnetic tracking system 30 or a combination of the electromagnetic tracking system and additional hardware such as an Arduino Uno (Arduino, Turin, Italy). A computing device 23 such as a laptop or tablet computer may be operatively connected to the electromagnetic tracking system 30. A display 24 may also be operatively connected to the computing device 23. In one embodiment, the computing device 23 may be a laptop, notebook, or tablet computer with the display 24 being an associated display of the computing device 23. The computing device 23 may be programmed or otherwise configured to receive tracking information from the electromagnetic tracking system 30 and use the tracking information, including positions of the bone shaft 12 and bone fragments 14 in order to generate virtual fluoroscopic images for viewing on the display 24. Different views may be provided such as a lateral image 36 and an anteroposterior image 28. The views may be generated on request of a user or in real-time. In addition, information from the electromagnetic tracking system may be stored on a non-transitory computer readable storage medium of the computing device 23 for later use or analysis including for use in evaluating performance by the surgical resident or other user of the system 10.

Note that the system 10 need not include any type of special surgical instruments or tools. In this system, position and/or orientation of the surgical instruments need not be tracked. Instead, a conventional physical surgical instrument may be used such as a surgical wire or a tenaculum. This may be advantageous in training because the surgical resident will be using the same type of surgical instrument they would use in an actual surgery as opposed to some type of virtual surgical tool or physically modified surgical tool. This may also be advantage as it allows individuals to train with different surgical instruments. Alternatively, a surgical tool 17 such as a tenaculum may be used which may have one or more sensors attached where it is desirable to track position and/or orientation of the surgical instruments.

It is to be further understood that not all bone fragments need be connected to a sensor 16. For example, one or more of the bone fragments may be in a fixed position relative to the emitter 20 so that it need not be tracked individually. For example, one long, big piece of bone may be in a fixed position in the simulator and the fragments may be tracked and moved with respect to the fixed bone.

Figure 2:
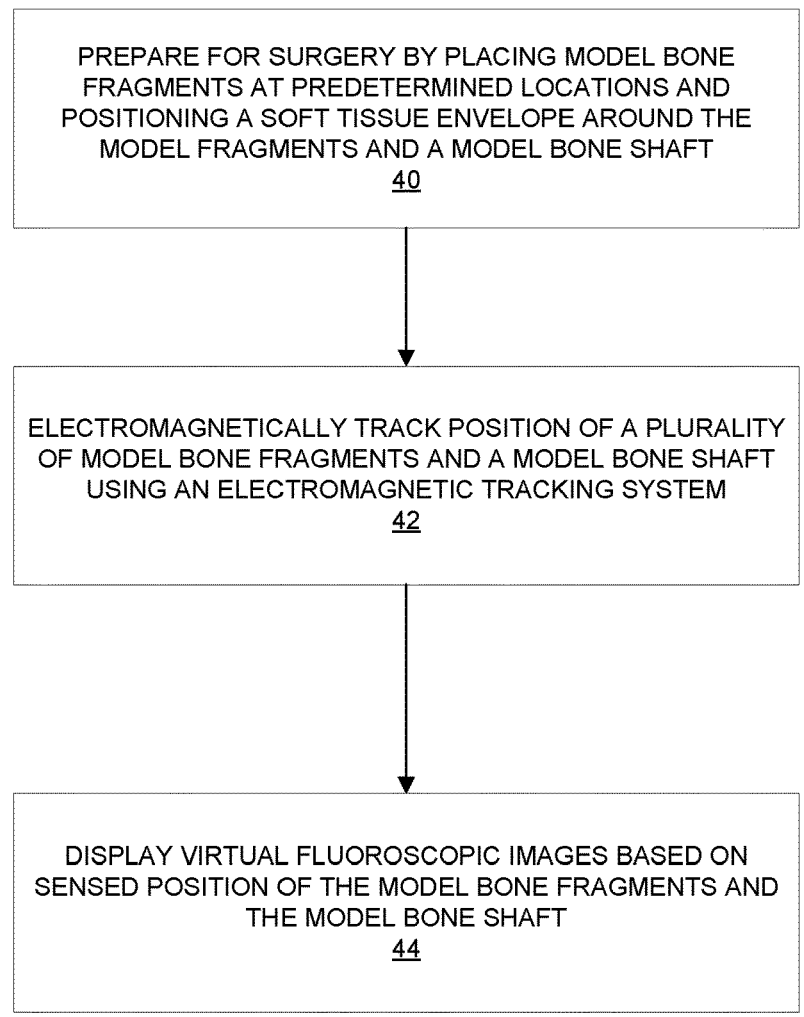
FIG. 2 is a flow chart illustrating one example of a method.

FIG. 2 illustrates one example of a method. In step 40, the method involves preparing for surgery by placing model bone fragments at predetermined locations and positioned a soft tissue envelope around the model bone fragments and a model bone shaft. The predetermined locations may be selected to practice or test specific surgical skills of a surgical resident. It is contemplated that the system may allow an instructor or other individual preparing the surgery simulator to select different scenarios and each scenario may have specific locations. The tracking system may be used in preparation for the surgery to assist in placing the model bone fragments at desired locations.

In step 42, the method provides for electromagnetically tracking position of a plurality of model bone fragments and a model bone shaft using an electromagnetic tracking system. In addition, the position and orientation of a surgical tool may also be tracked with the electromagnetic tracking system. The electromagnetic tracking system may include an emitter and sensors. In operation, the emitter may generate an electromagnetic field and changes in the electromagnetic field may be sensed at the sensors 16 in order to determine position and orientation of the sensors 16. The sensors 16 may also be operatively connected to the computing device 22 which may compute position and orientation of each of the sensors. In addition, the computing device 23 may store information regarding the size and shape of the bone shaft 12 and each of the bone fragments 14 as well as the position of each sensor attached to the bone shaft 12 and the bone fragments 14. This information may then be used in generating virtual fluoroscopic images including a lateral image 26 and an anteroposterior image 28.

In step 44, the virtual fluoroscopic images which are based on sensed position of the model bone fragments and the model bone shaft may be displayed and viewed on a display. This may be in response to a user requesting images or may be performed in real-time.

Figure 3:
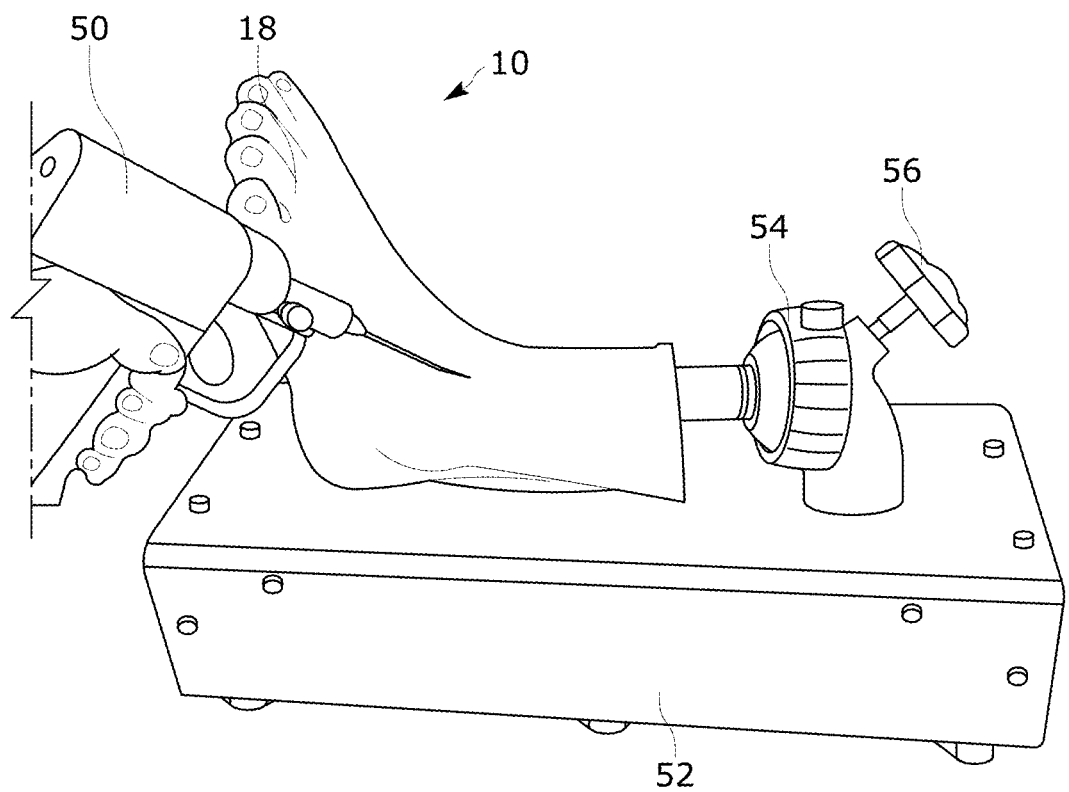
FIG. 3 is another view of a system for simulating surgery.

FIG. 3 further illustrates an embodiment of the system 10. As shown in FIG. 3, a surgical resident may use a conventional surgical instrument 50 such as a surgical wire when performing a simulated surgery. A soft tissue envelope 18 surrounds the model bone shaft and model bone fragments and thus these are not seen directly by the surgical resident but instead using the virtual fluoroscopic images. A platform 52 is shown. A ball-and-socket joint 54 is shown along with a locking knob 56.

Figure 4:
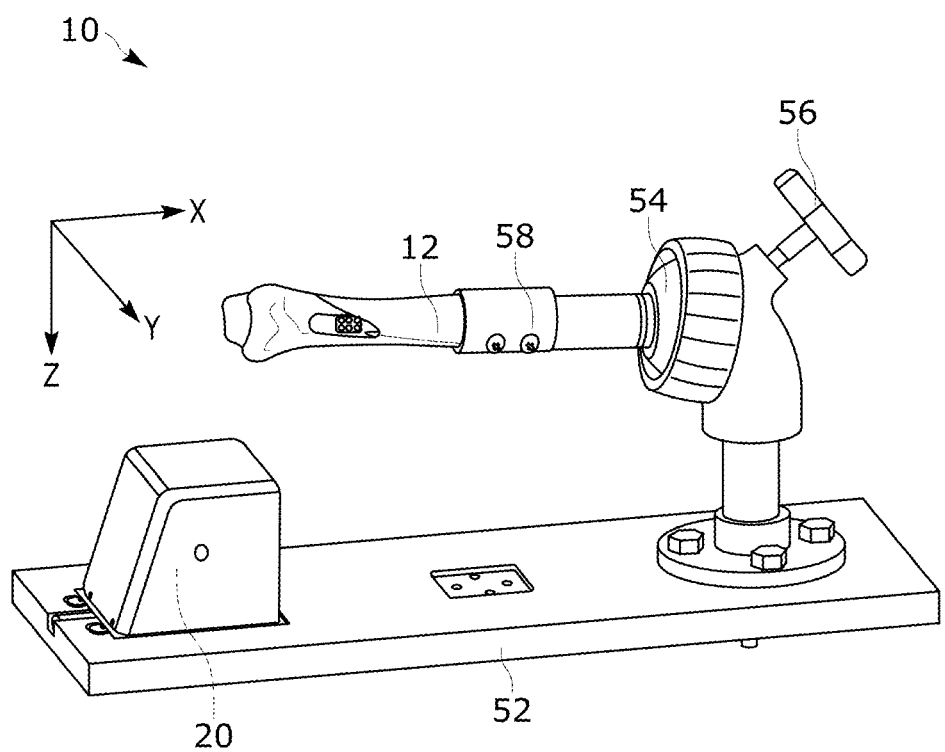
FIG. 4 is another view of the system for simulating surgery.

FIG. 4 is another illustration of an embodiment of the system 10. As shown in FIG. 4, a platform 52 is provided. An emitter 20 (a part of the electromagnetic tracking system) may be operatively connected to the platform 52. A tibia clamp 58 is shown for operatively connecting to the model bone shaft 12. The ball-and-socket joint 54 and the locking knob 56 are also shown. The simulator's synthetic tibial shaft, tibial fragments, and soft tissue envelope may be based on a commercial tibial plafond fracture model (Sawbones, Vashon Island, WA).

The positions of the synthetic bone fragments and the intact tibial shaft may be monitored using an electromagnetic tracking system (Ascension Technology, 3D Guidance trakSTAR, Shelburne, VT), which includes an emitter and four sensors. The tracking hardware may be encased in a customized, plastic box and integrated mount for the model as shown in FIG. 4. The electromagnetic tracking system may be set-up in a compact work area, it can sense position with 6 degrees of freedom through solid objects, and it can record multiple positions in real time. This is accomplished via small wired sensors that register their location in a generated electromagnetic field. These sensors may be mounted in specially designed keys that attach to the models they track. The key and sensor assembly is shown in FIG. 5.

Figure 5:
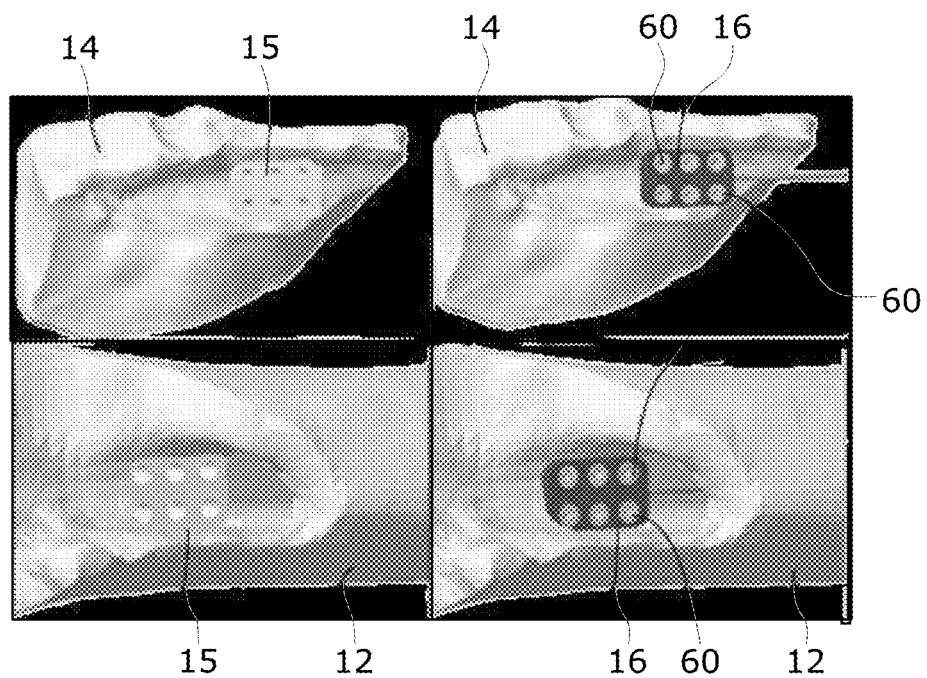
FIG. 5 illustrates sensors of the electromagnetic tracking system precisely affixed to bone fragments.

FIG. 5 illustrates a bone fragment 14 and a bone shaft 12. Keys 15 are shown into which sensors 16 may be placed. The key 15 is firmly mounted to the sensors through a clamshell design with tapped holes in the bottom half that nylon bolts thread through. This allows for the sensors to be calibrated individually before incorporating them with the models they track. These keys fit onto the fracture model by a press fit insertion into a designated slot. Because this construct creates a rigid body between the sensor and the object it is tracking, the exact location of the tracked object may be determined within six degrees of freedom. These keys may also be placed on surgical tools such as a tenaculum if desired.

Figure 6:
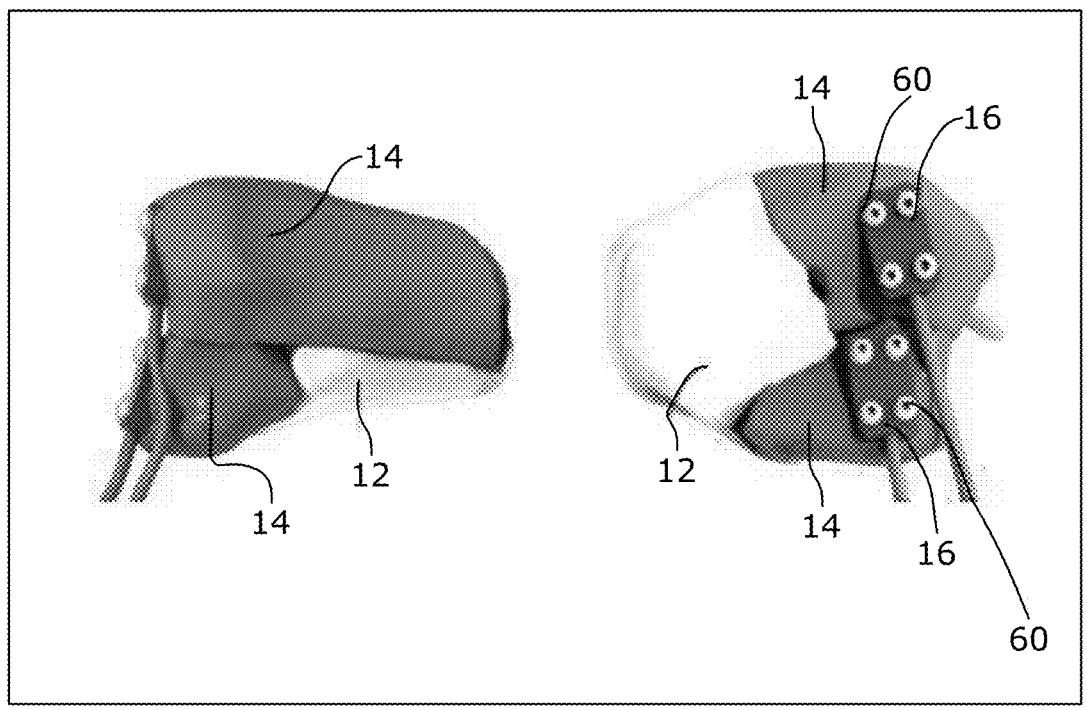
FIG. 6 illustrates another example of sensors of the electromagnetic tracking system precisely affixed to bone fragments.

FIG. 6 further illustrates bone fragments 14 and a bone shaft 12. Sensors 16 are shown with one sensor positioned on each of the model bone fragments 14. Note that the sensors 16 are secured to the model bone fragments 14 using four screw-in key connectors which mate with slots in the model bone fragments 14. This allows the sensors 16 to be securely affixed to each of the model bone fragments 14, yet still allows the sensors 16 to be removed so that the same electromagnetic tracking system may be used in different applications such as by attaching the same sensors 16 to different model bone fragments. Moreover, this type of mounting allows the position of the sensor 16 on each of the bone fragments or bone shaft to be known by the system and be in a precise location. The sensors may be precisely affixed to each of two model bone fragments and to the tibial shaft using a screw-in key and slot configuration.

Thus, the screw-in key and slot configuration allow the mounting of the sensors synthetic bone fragments in a known orientation. Once a key with the embedded sensor is calibrated it can then be quickly swapped to new fragments or tools, which all accept the same key. This allows for efficient replacement with new fragments, or for a multitude of different fractures to be used without recalibration.

A clamping mechanism connects the proximal end of the synthetic tibia to a ball-and-socket joint which allows the surgeon to rotate and lift the foot within the working frame. A screw knob secures the desired position. The emitter (hidden under the simulator housing) produces an electromagnetic field. The tracking system can determine the 6-degree-of-freedom position of the individual sensors within this field. A soft tissue envelope is then placed around the bone model, hiding it from plain view, and the fragments are appropriately displaced to pre-determined locations so the surgeon can re-align them.

The electromagnetic sensors may offer a large workspace, constituting a cube with sides of 20×28×30 cm from the center of the emitter. Within this workspace, the manufacturer claims that the sensor error is less than 1.4 mm. The position accuracy diminishes as the sensors get farther from the electromagnetic source. This workspace comfortably accommodates the sensors affixed to the fragments and the tibial shaft while still allowing for the user to adjust the model during use.

Thus, this tracking system allows for the user to move the entire model as they please, allowing for realistic manipulation of the simulated patient. A ball and socket with a locking mechanism allows for the user to lock the model into position. This mounting system also has channels to hide and protect the sensor wires.

Figure 7:
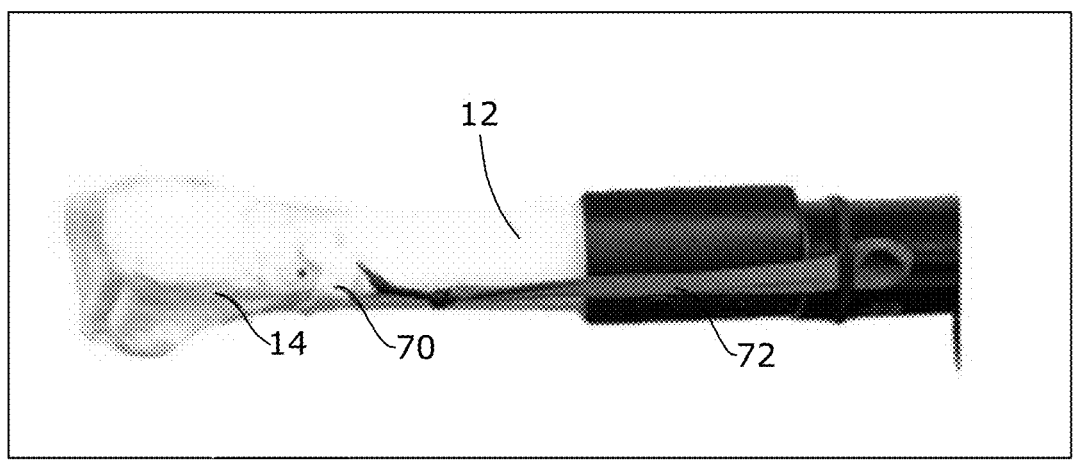
FIG. 7 illustrates a bone model with a reset feature.

In some embodiments, a re-set feature may be added. FIG. 7 illustrates one example of a re-set feature. When the fracture is to be re-set in the same starting location between trials, allowing for comparison across trials and for the user to have repeated practice with the same fracture, a special re-set feature has been added to the fracture model. A starting location may be determined. A loop may be generated from the face geometry of the free-fragment in this position. This loop 70 may then be attached to the base-fragment 12. A rubber band or other elastomeric member 72 may then be attached to the free-fragment 14 and pass through the loop 70 in the base fragment 12, finally attaching to the base of the mounting bracket. The force from the rubber band or other elastomeric member 72 pulls the free fragment back into this loop 70, holding it in the starting position.

Figure 8:
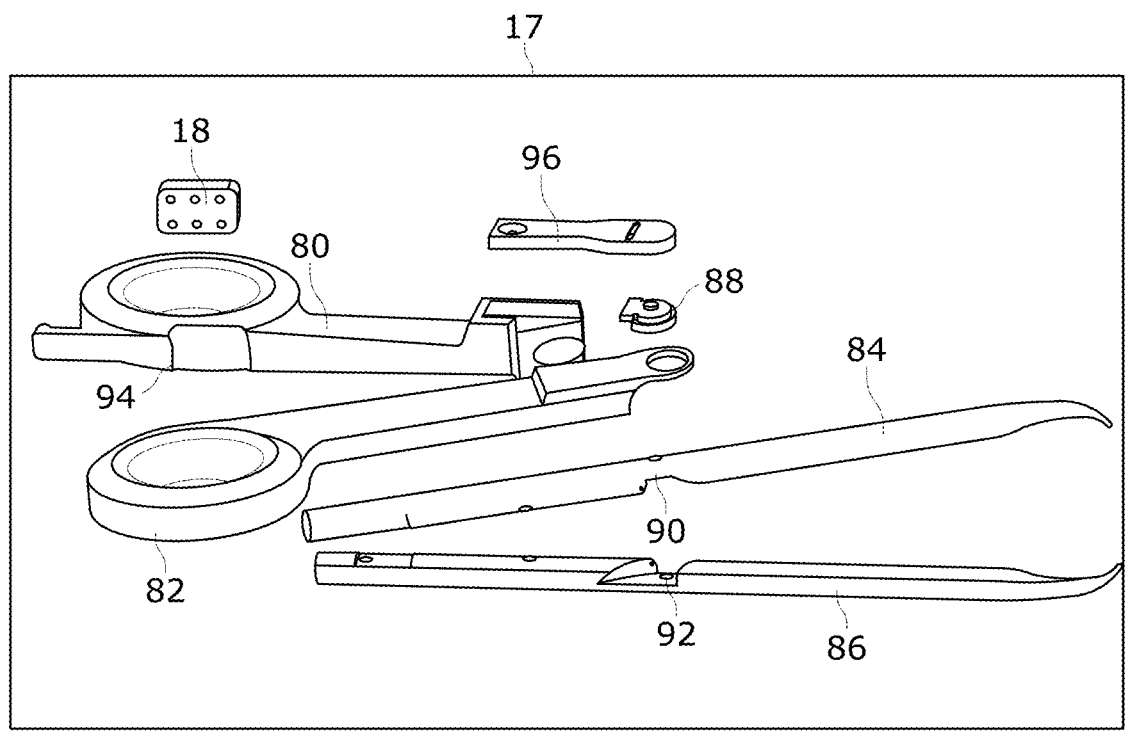
FIG. 8 illustrates an exploded view of a surgical instrument.

As previously mentioned, surgical tools may be tracked. FIG. 8 illustrates an exploded view of one example of a surgical tool (a tenaculum) 17 which may be used. The body including handles 80, 82 may be constructed out of ABS plastic, and the tool may be held together with nylon bolts (not shown). The sensor 16 may be positioned on one of the handles 94 to align with a slot 94.

It is advantageous to construct the surgical tool 17 from plastic as opposed to metal in order to improve accuracy associated with the electromagnetic tracking system. However, it may be advantageous to form the tines 84, 86 of the tenaculum 17 from metal in order to be strong enough to withstand the forces imparted on it during use. Tenaculum tines 84, 86 are shown which may be made from stainless steel or other metal which is sufficiently strong and which limits distortion of the electromagnetic field associated with the electromagnetic tracking system.

Angle between the two tines 84, 86 can be determined using a potentiometer 88 or other type of sensor. Alternatively, multiple electromagnetic tracking sensors (e.g. one associated with each tine) may be used in which case a potentiometer would not be needed. As shown, the two tines when assembled may rotate about a pivot point associated with a screw (not shown) and the total rotation may be limited by the shape of slots 90, 92. Limiting the total rotation may assist in tracking. As shown, the total rotation is limited to about 55 degrees although other limits may be used. The potentiometer 88 may be attached to a removable key 96 which allows the potentiometer 88 to be replaced if needed.

Figure 9:
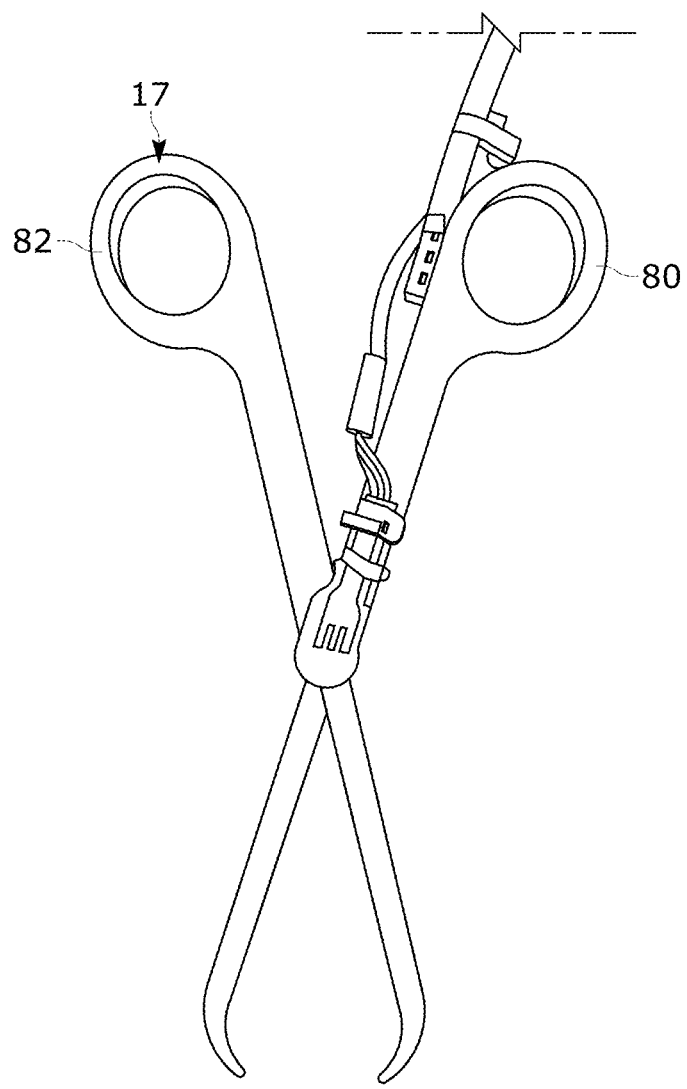
FIG. 9 illustrates a surgical instrument.

FIG. 9 illustrates a view of an assembled tenaculum 17.

The code that has been generated for this simulator was designed with the intent to be intuitive, fully autonomous, and user friendly. This was done to achieve the design intent of keeping the simulator simple, intuitive, and to eliminate the need for external resources to run the simulator or score the performance. In order to simplify the design, all the code required to run the simulator, interface with the tracking system, and score the user playback has been written in MATLAB. It is to be understood, however, that more complicated design methodologies may be used and any number of computer languages or environments may be used.

At the start of a trial a continuous sampling of the sensor positions begins with a sampling rate of 80 measurements/second. The MATLAB script then requests the latest position measurements from the sensors in the form of quaternions when necessary. The quaternions are then converted into transformation matrices in the form of:

$$T = \begin{bmatrix} R_{11} & R_{12} & R_{13} & T_x \\ R_{21} & R_{22} & R_{23} & T_y \\ R_{31} & R_{32} & R_{33} & T_z \\ 0 & 0 & 0 & 1 \end{bmatrix} \quad (1)$$

In order to meet the design criteria of sub-millimeter accuracy, a calibration transformation matrix is then applied to the sensor attached to the free-fragment to get the corrected location for the sensor. The calibration matrix effectively subtracts the error matrix E from the sensor transformation matrix T to get the corrected transformation matrix $T_c$ for the free fragment following:

$$T_c = E^{-1} * T \quad (2)$$

The transformation matrices are then used to locate and draw STL models in the virtual environment that correspond to the physical models. The STL models have been designed such that their reference frames correspond to the zero point and reference frame of the sensors that are attached to them, thus once the sensors have been calibrated, the virtual models for the base fragment and free fragment do not need further offsets. This was done to save machine resources, increase the speed of the software, and maintain the simplicity of the code. Of course, any number of alternative implementations may be used.

In order to locate the tenaculum used in the simulator a second offset has to be generated to fully locate it. This is necessary because, while one tine has the sensor affixed to it is located using the same technique for the base fragment, the other tine of the tenaculum is found through the potentiometer that has been used in the design. Locating the tine that does not have the sensor directly attached to it is performed by measuring the voltage from the potentiometer and converting that reading to an angle. Measuring the voltage from the potentiometer is performed through an Arduino (or other computing devices) which acts as a slave to the main MATLAB program. The voltage difference can be mapped to the angle of rotation between each tine in radians through a linear regression following:

$$\text{radians} = \frac{\Delta\theta}{\Delta V} * V_x + \left(\theta_{open} - \frac{\Delta\theta}{\Delta V} * V_{open}\right) \quad (3)$$

Where $V_x$ is the reading provided by the Arduino or other computing device, $\theta_{open}$ is the maximum open angle in radians between the tines, $V_{open}$ is the voltage at this position, $\Delta\theta$ is the total difference between the maximum open and closed positions, $\Delta V$ is the difference in voltage between the maximum and minimum open positions, and $V_x$ is the voltage that is sampled during data collection. A rotation matrix is then created from this angle which resembles that of Equation 1, however the translation data is set to zero. This rotation matrix is then multiplied by the offset transformation matrix from the tool sensor to the pivot point between the two tines of the tenaculum. This resulting transformation matrix is then applied to the tine, which is set as a child to the parent tine with the sensor.

Figure 10:
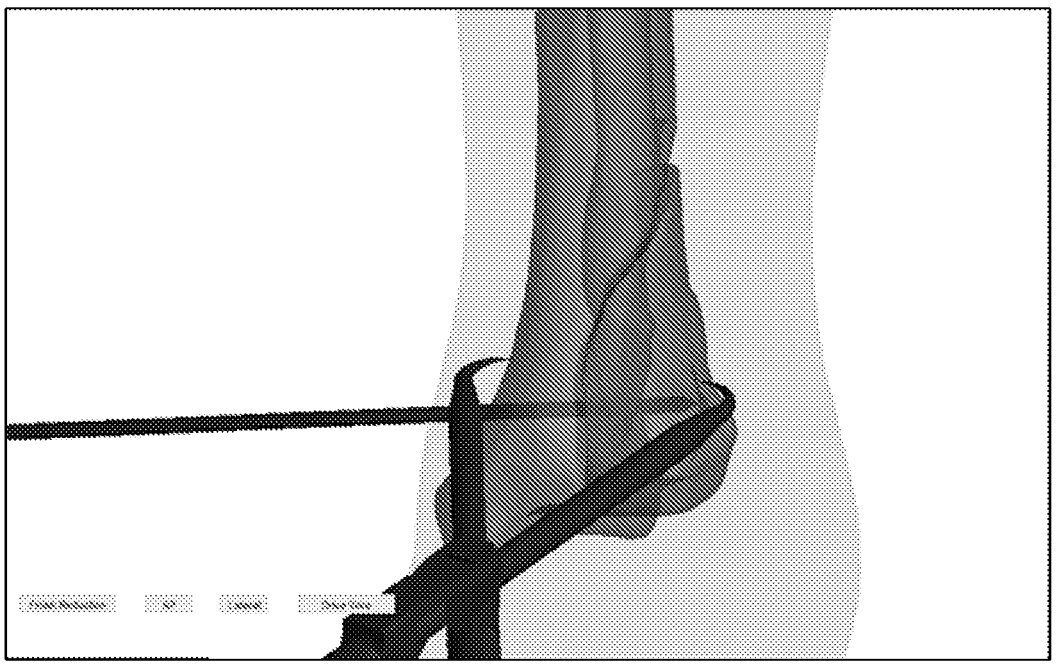
FIG. 10 is a digital fluoroscopic view of sample reduction.

A typical reduction involves locking the tenaculum when a reduction is achieved and then placing k-wires to hold the reduction. Because there is only one tool in this simulator and this tool does not have a locking mechanism, some digital techniques have been employed to simulate the locking and k-wire placement steps of the procedure. When the user achieves an acceptable reduction using the tenaculum they alert a second user to click a button, where the position of the tool and fragment then become locked with respected to the base fragment transformation. This is done by multiplying the inverse of the base fragment sensor transformation matrix by the transformation matrix of the sensor attached the tenaculum and to the free fragment in the same manner as Equation 2. The base fragment and the tenaculum are then set as children to the parent, which in this case is the base fragment. At this point the transformation matrices for the tenaculum and the fragment are no longer updated and follow the base fragment as it is moved. The physical tenaculum then changes function to representing a virtual K-wire and the first K-wire digital model is made visible. The virtual K-wire is placed using the sensor affixed the tenaculum and has the same reference frame as this sensor, making the wire line up with the tine of the tenaculum that has the sensor affixed to it. The virtual wire extends roughly 40 mm beyond the tip of the tenaculum, which allows for it to be rendered inside of the fracture model. This simulates placing a wire into a fracture. A figure showing a sample reduction and a subsequent wire placement can be seen in FIG. 10.

The process of sampling, applying the offsets, rendering, and recording the positional data loops continuously during use at a sampling frequency of 7 Hz. The data is recorded in the form of a 4 row by 17 column by n matrix, where n is the loop iteration. The matrix consists of three 4 by 4 matrices that make up the position of the three sensors used in the simulator. The $17^{th}$ column records the current time that each sampling period is taken in, the view that the user has requested (AP or Lateral), and the number of wires that have been used for pinning the reduction. After the user has completed the experiment, this matrix is then saved to the unique sub directory that has been created during the start of running the program.

The code written meets the initial design criteria of generating realistic imaging where the user can recognize key identifying landmarks on the fracture model, tracking multiple objects in real time and saving this data. This code also meets the functionality constraints by not requiring an external computer to run the simulator or to save the data gathered during experimentation. Further, this code has all been written in the same language, keeping the system simple to use and efficient. Of course, numerous alternatives are contemplated for providing the same or similar functionality.

It is also to be understood that calibration may be provided in various ways. For example, the trakSTAR system provides data for the sensor rotation in terms of a rotation matrix, but it can also report in Euler angles; roll, pitch and yaw. Due to the geometry of the sensor, the yaw and pitch will be held constant, orthogonal to one another and along the axial direction of the sensor, but the roll is undefined as it is a rotation about the sensor axis. Because the sensor is cylindrical, this orientation is not clear by looking at the sensor alone.

Figure 11:
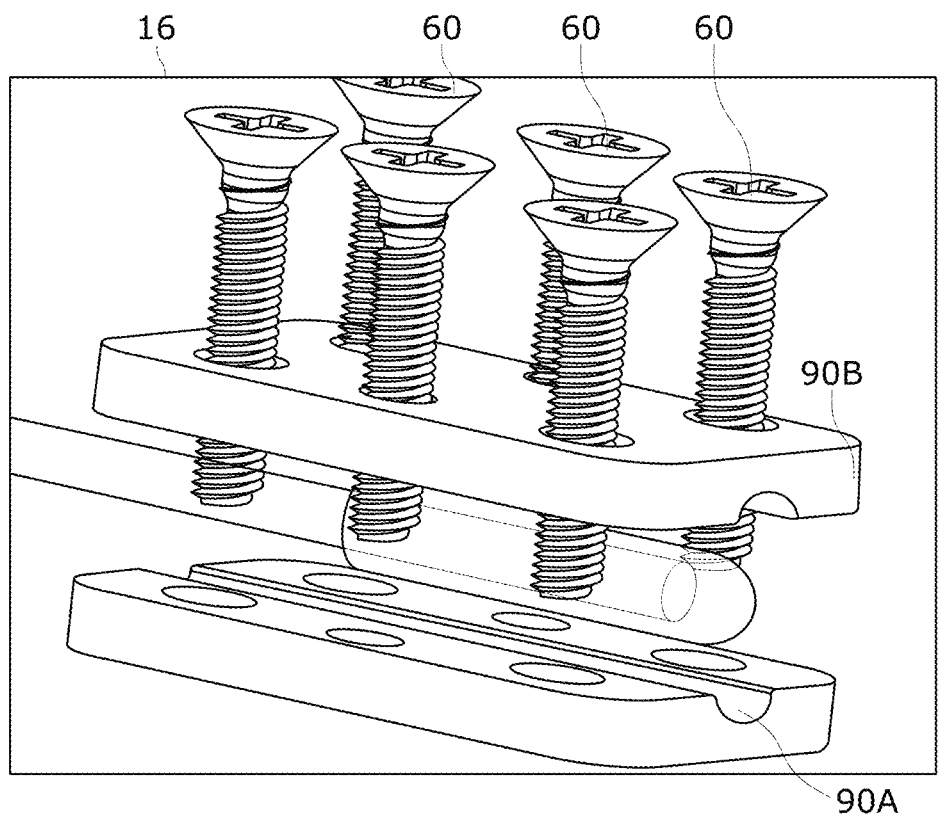
FIG. 11 illustrates a view of a sensor.

To define the roll, first a sensor is locked into a key by screwing the two halves 90A, 90B of the key together, clamping the sensor in the middle as shown in FIG. 11. Once the key is fixed, the bottom face provides a datum plane to reference off. This key is then loaded onto the top face of a calibration block that has a perpendicular bottom face. This calibration block is then placed into a slot milled into the base of the simulator. Because a slot that holds the transmitter has also been milled into the base, the transmitter, calibration block, and key should all be held with the yaw and pitch planes in parallel alignment. Using the calibration GUI that interfaces with the trakSTAR system, the roll angle can be measured and reported. Using this angle, we can call a function on the trakSTAR that offsets the roll angle to zero, locking the sensor into alignment with the key. Once a sensor has been calibrated to an individual key, it will remain in that orientation unless the key is removed from the sensor, in which case it will need to be re-calibrated. Thus, course calibration may be performed. Of course, it is to be understood that different calibration procedures may be used with different sensors.

Despite performing this course calibration, there will still be inaccuracies in the model due to machining error, distortion from the local environment, inaccuracies in the tracking system, imperfect coarse calibration, and error from the 3D printing technology used. The error is then further reduced by implementing an offset in the MATLAB code. This is done again using the calibration GUI. The following calibration procedure finds the error of the free fragment in relation to the base fragment. This is done because it is impossible to measure the ideal positions of the two fragments in the global reference frame of the transmitter, and because the most important relationship in the simulator is that of the free fragment to the base fragment. This calibration is performed by placing the calibrated sensors (held in their keys) on the two fragments and then by holding the fragments in a reduced state while simultaneously clicking the Find CT button in the calibration GUI. The offset transformation matrix is found by determining the amount of error between the held reduction from the ideal reduction measured while generating the STL models. The error is measured as the difference in the position of the free fragment with respect to the base fragment. First the fragment position with respect to the base fragment is found by the following equation:

$$T_{free\ to\ base\ frag} = T_{base\ frag}^{-1} * T_{free\ frag} \quad (4)$$

where $T_{free\ to\ base\ frag}$ is the resultant distance between the base fragment and the free-fragment. Then this resultant transformation matrix is multiplied by the inverse of the ideal transformation matrix between the base fragment and the free fragment $T_{ideal}$, which is found in CREO. The equation for this is:

$$T_c = T_{ideal}^{-1} * T_{free\ to\ base\ frag} \quad (5)$$

This equation then gives the error transformation matrix $T_c$, which is copied and pasted into the MATLAB code. This error matrix is then applied to the free fragment after every sampling period by the following:

$$T_{corrected\ free\ frag} = T_{free\ frag} * T_c^{-1} \quad (6)$$

Which is essentially subtracting the error from the reading each time. The amount of error using this correction matrix is usually a total displacement of around 1.5 mm and a total rotational error of roughly 1 degree. These parameters also fall within the trakSTAR reported accuracy from each sensor. It is important to note that while the accuracy of each sensor might be off by this amount, the precision remains high. For this reason, using this final calibration, the sensors can find their relationship to one another in a sub millimeter range.

To implement the potentiometer into the simulator, a calibration procedure is performed to determine the voltage to rotation relationship. This procedure does not have a built-in function; however, the implementation is still relatively straight forward. The voltage is sampled with the tenaculum in the fully closed position, and again in the fully open position. These values are then coded into the MATLAB script. Because the tool full open and full closed range is known through pre-determined manufacturing techniques and have been confirmed through measurements, a linear relationship can be formed between the voltages and the known angles at the open and closed positions. Of course, it is to be understood that what is described regarding such calibrations is illustrative only as any number of other calibration procedures may be performed depending upon the specific make and model of sensors, their size and shape, and other factors.

Figure 12:
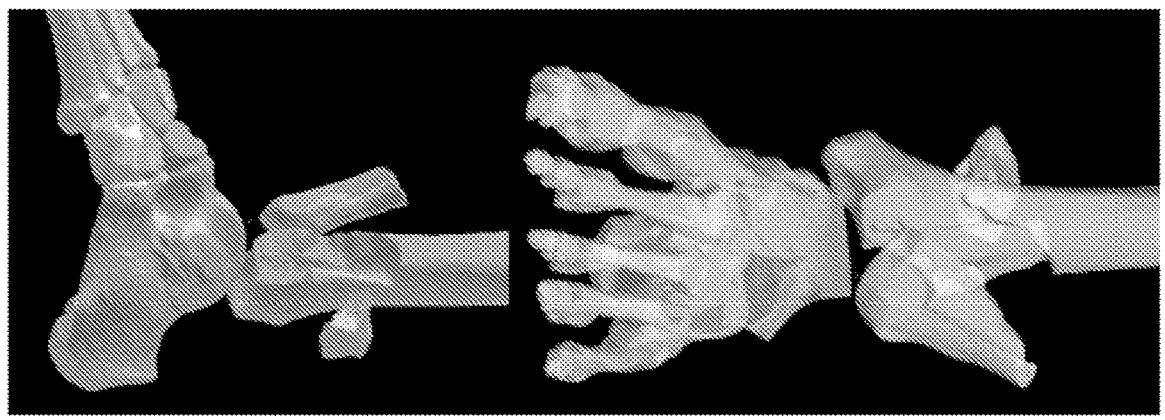
FIG. 12 illustrates virtual fluoroscopic images of an exaggerated fracture with dislocated fragments in two common viewing angles.

FIG. 12 illustrates an example of a screen display such as may be displayed on a display. The screen display shows virtual fluoroscopic images such as a lateral image and an anteroposterior image. These images may be generated using location information from the electromagnetic tracking system as well as known information about the model bone fragments including size, shape and location of the sensors on the bone fragments.

In addition, the computing device may be configured to incorporate realistic virtual x-ray simulation to accurately account for bone density. This may be achieved by providing accurate shading of the bone to increase the reality of the simulation. This assists students to learn how to read the shading of the bones and develop an understanding about how the orientation and overlap changes this.

FIG. 7 illustrates a reference board used for testing. Based on clinical guidelines for success in this surgery, the fragment positions must be tracked within 1 mm. To quantify the fragment tracking precision, we constructed a fixture to move the sensors through a space slightly larger than the soft tissue envelope. The fixture consisted of a keyed cube, which holds three of the sensors, a reference board with four precisely located cube locators spaced 10 cm apart, and a set of non-metallic clamps to position the plane. Using the sensor readings, the reference board was carefully aligned to be parallel to one of the emitter's primary axes. The calibration cube, with the three sensors attached, was then moved between three or four indents of the reference board, spanning a region larger than the needed workspace. Relative measurements of the distance from the starting indent could then be compared against the known spacing of the indents.

The sensor error was estimated for movements along each axis in nine trials, three repetitions along each of 3 axes. The first position on each trial, the position closest to the emitter (indent 1), was used as reference. Each subsequent indent location on the board was adjusted by subtracting the average position of the reference. The error of the three sensor reports and their standard deviation along the principal axes were reported for each trial, representing the relative bias and precision of sensor readings in the selected directions.

FIG. 8 presents the bias and precision of the relative sensor movements in the x and y directions within the workspace of the simulator. Error bars represent the standard deviation of the values from three repeated trials. The workspace for the sensors in the simulator is within 100 mm of the trials reported in FIG. 8. The bias in this region is less than 1 mm and the standard deviation is better than 0.25 mm, performance sufficient for the alignment of articular fragments. These results confirm the viability of the new simulator for creating a new, useful educational opportunity for surgical residents and introducing a technical platform that may support other high precision surgical simulations as well.

The present invention addresses limitations presented in the previous imagery-based simulator, where the objects to be tracked had to be visible and with a clean viewing path between the object and the camera. The electromagnetic system is not hindered by line-of-sight requirements because the electromagnetic field can penetrate solid material. This simulator also improves upon the first electromagnetic system through the use of the key and slot system devised for placing the sensor on the object to be tracked, allowing the user to manipulate the whole model as well its fragments independently without losing their locations.

This simulator of the present invention will allow residents to practice percutaneous reduction using a repeatable model that can also be easily adapted to other fracture models using the novel key and slot sensor attachment. This work successfully increases the number of different surgeries that can be simulated using our physical model and virtual reality platform and addresses limitations in previous generations of surgical simulators that prevented them from being able to reproduce a fracture reduction surgery.

Although a particular configuration for the system has been shown and described in detail, it is to be understood that other surgical skills may be taught, that different bone models may be used, that different sizes and shapes of bone fragments may be used as well. It is to be further understood that different types of electromagnetic tracking systems may be used, sensors may be affixed in alternative ways, sensors may be positioned in other locations, and other variations are contemplated. For example other implementations are contemplated where sensors are added to surgical instruments so that one does not need to track every dynamic component in the tool.

In addition, in some embodiments, other types of tracking systems may be used such as optical tracking. For example, it is to be understood that functionality of the computing devices may be combined, or functionality of a single computing device may be spread across a plurality of computing devices.

It is to be further understood that instead of electromagnetic tracking, other types of tracking may be used alone or in combination with electromagnetic tracking. Other types of tracking may include generating images and then processing the images using image processing. Where image processing is used, images of the model bones and model bone fragments may be generated in various ways including from radio signals, use of radar sensors, or other types of sensing. The different bone fragments may have markings or other properties associated with each of them to assist in locating and identifying position and orientation of them. In another alternative, potentiometers or capacitance sensors may be used to detect position.

The system may be used in various ways including to practice surgical skills as well as to assess surgical skills of an individual. It may further be used to compare surgical techniques for a particular fracture pattern and to evaluate treatment approaches such as different surgical designs.

The invention is not to be limited to the particular embodiments described herein. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

What is claimed is:

1. A system for simulating surgery, comprising:
an electromagnetic tracking system comprising an emitter and a plurality of electromagnetic sensors; and
a plurality of model bone fragments, each of the model bone fragments operatively connected to one of the plurality of electromagnetic sensors;
wherein the electromagnetic tracking system provides for locating position and orientation of each of the plurality of model bone fragments.

2. The system of claim 1 further comprising a display system in operative communication with the electromagnetic tracking system for displaying virtual fluoroscopic images based on a sensed position of the model bone fragments.

3. The system of claim 2 further comprising a model bone shaft having an additional electromagnetic sensor associated therewith.

4. The system of claim 3 further comprising a soft tissue envelope for positioning around the plurality of model bone fragments and the model bone shaft.

5. The system of claim 4 wherein the model bone shaft is operatively connected to a ball-and-socket joint to allow for positioning of the model bone shaft.

6. The system of claim 1 wherein the surgery is a percutaneous articular fracture reduction surgery and wherein the model bone fragments are model tibial fragments.

7. A method for simulating surgery, the method comprising:
electromagnetically tracking position and orientation of a plurality of model bone fragments and a model bone shaft using an electromagnetic tracking system; and
displaying virtual fluoroscopic images based on sensed position of the model bone fragments and the model bone shaft.

8. The method of claim 7 wherein the electromagnetic tracking system comprises an emitter and a plurality of electromagnetic sensors, each of the electromagnetic sensors attached to one of the model bone fragments or the model bone shaft.

9. The method of claim 7 wherein the electromagnetically tracking position occurs while a user manipulates one or more of the plurality of model bone fragments using a physical surgical instrument.

10. The method of claim 9 wherein the physical surgical instrument is from a set consisting of a surgical wire and a tenaculum.

11. The method of claim 7 further comprising preparing for the surgery by placing the model fragments at predetermined locations and positioning a soft tissue envelope around the plurality of model bone fragments and the model bone shaft.

12. The method of claim 7 wherein the position is a 6-degree-of-freedom position.

13. The method of claim 7 wherein the surgery is a percutaneous articular fracture reduction surgery and wherein the model bone fragments are model tibial fragments and the model bone shaft is a model tibial shaft.

14. The method of claim 7 wherein the fluoroscopic images include a lateral image and an anteroposterior image.

15. The method of claim 7 further comprising receiving a request from a user to display the virtual fluoroscopic images and wherein the displaying the virtual fluoroscopic images is responsive to the request.

16. A method for simulating surgery, the method comprising:
providing a system for simulating surgery, the system comprising an electromagnetic tracking system comprising an emitter and a plurality of electromagnetic sensors and a plurality of model bone fragments and a model bone shaft, each of the model bone fragments operatively connected to one of the plurality of electromagnetic sensors or the model bone shaft;
electromagnetically tracking position of the plurality of model bone fragments and the model bone shaft using the electromagnetic tracking system; and
displaying virtual fluoroscopic images based on sensed position of the model bone fragments and the model bone shaft.

17. The method of claim 16 wherein each of the model bone fragments is removably attached to one of the plurality of electromagnetic sensors.

18. The method of claim 16 wherein the electromagnetically tracking position occurs while a user manipulates one or more of the plurality of model bone fragments using a physical surgical instrument.

19. The method of claim 16 wherein the electromagnetically tracking position occurs while a user manipulates one or more of the plurality of model bone fragments using a physical surgical instrument.

20. The method of claim 16 further comprising preparing for the surgery by placing the model fragments at predetermined locations and positioning a soft tissue envelope around the plurality of model bone fragments and the model bone shaft.

* * * * *